United States Patent
Potier et al.

(10) Patent No.: US 10,563,246 B2
(45) Date of Patent: Feb. 18, 2020

(54) MICROFLUIDIC DEVICE FOR PRODUCTION AND COLLECTION OF DROPLETS OF A FLUID

(75) Inventors: Marie-Claude Potier, Paris (FR); Patrick Tabeling, L'hay les Roses (FR); Luce Dauphinot, Voulangis (FR); Nadege Bois, Cesson (FR); Fabrice Monti, Saulx les Chartreux (FR); Pascaline Mary, Cambridge, MA (US)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 212 days.

(21) Appl. No.: 13/876,960

(22) PCT Filed: Oct. 3, 2011

(86) PCT No.: PCT/EP2011/067229
§ 371 (c)(1),
(2), (4) Date: May 28, 2013

(87) PCT Pub. No.: WO2012/042060
PCT Pub. Date: Apr. 5, 2012

(65) Prior Publication Data
US 2013/0236901 A1   Sep. 12, 2013

(30) Foreign Application Priority Data
Oct. 1, 2010   (EP) .................................... 10290526

(51) Int. Cl.
| | | |
|---|---|---|
| *C12Q 1/68* | (2018.01) | |
| *C12Q 1/6806* | (2018.01) | |
| *C12Q 1/6813* | (2018.01) | |
| *C12Q 1/6844* | (2018.01) | |

(52) U.S. Cl.
CPC ......... *C12Q 1/6806* (2013.01); *C12Q 1/6813* (2013.01); *C12Q 1/6844* (2013.01)

(58) Field of Classification Search
None
See application file for complete search history.

(56) References Cited

U.S. PATENT DOCUMENTS

| | | | | |
|---|---|---|---|---|
| 2002/0033939 A1* | 3/2002 | Hansen | .................. | G01N 15/14 356/73 |
| 2005/0136534 A1 | 6/2005 | Austin et al. | | |
| 2008/0003142 A1* | 1/2008 | Link et al. | .................. | 422/82.08 |
| 2009/0197248 A1* | 8/2009 | Griffiths | ................ | B01F 3/0807 435/6.11 |
| 2010/0086919 A1* | 4/2010 | McKeon | ................ | C07K 16/00 435/6.16 |
| 2010/0173394 A1* | 7/2010 | Colston, Jr. | ........... | B01F 3/0807 435/287.2 |

OTHER PUBLICATIONS

Mazutis, L., et al. Multi-step microfluidic droplet processing: kinetic analysis of an in vitro translated enzyme. Lab on chip, vol. 9, p. 2902-2908, 2009.*
J. Thormos et al. : "Droplet-based microfluidic platforms for the encapsulation and screening of mammalian cells and multicellular organisms". Chemistry and Biology, vol. 15, May 16, 2008 (May 16, 2008), pp. 427-437, XP002629099, p. 428-p. 430; figure 1, Cited ISR.
Chemistry and Biology, vol. 17, May 28, 2010 (May 28, 2010), pp. 528-536, XP002629100, pp. 530-531; figure 2, Cited in ISR.
Begolo et al.: "New family of fluorinated polymer chips for droplet and organic solvent microfluidics", published in Lab on a chip, issue 3, 2011, pp. 508-511, by The Royal Society of Chemistry. Accepted Oct. 28, 2010.
International Search Report, dated Jan. 20, 2012, from corresponding PCT application.

* cited by examiner

*Primary Examiner* — Suryaprabha Chunduru
(74) *Attorney, Agent, or Firm* — Young & Thompson

(57) ABSTRACT

A microfluidic device and method for producing and collecting single droplets of a first fluid, the device including a microfluidic platform having at least a droplet microchannel wherein is produced a flow of single droplets of the first fluid dispersed in a second fluid immiscible with the first fluid, the droplet microchannel having at least one inlet extremity and at least one outlet extremity for distributing the flow of droplets, the device further including:

a collection device including a plurality of receiving areas adapted to collect at least one of the droplets, elements for changing the relative position of the collection device and the outlet of the microfluidic platform, elements for controlling the flow of droplets, and elements for synchronizing the flow of droplets at the outlet of the droplet microchannel and the relative movement of the collection device with regards to the microfluidic platform.

28 Claims, 1 Drawing Sheet
Specification includes a Sequence Listing.

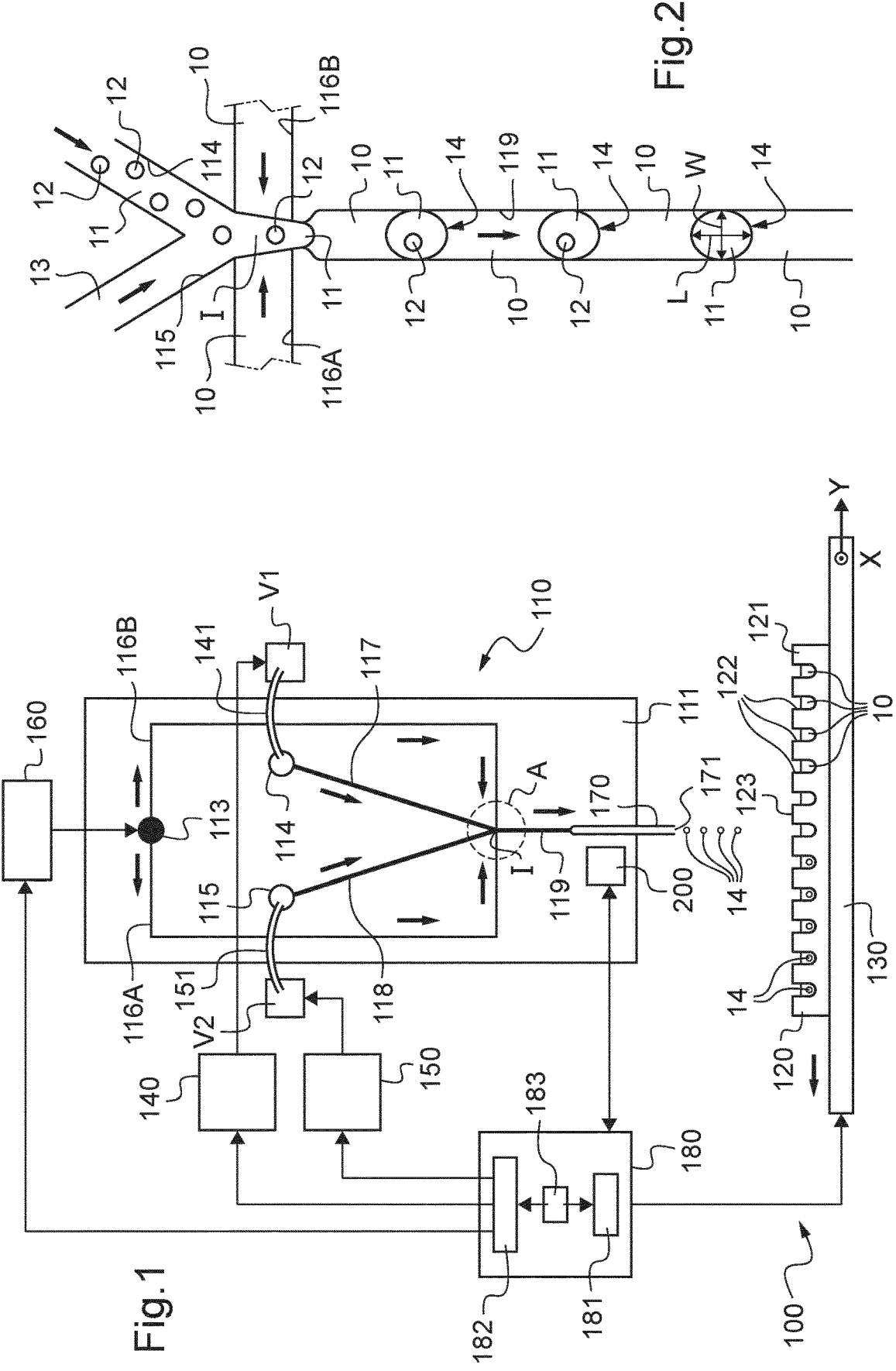

MICROFLUIDIC DEVICE FOR PRODUCTION AND COLLECTION OF DROPLETS OF A FLUID

FIELD OF THE INVENTION

The present invention relates to a microfluidic device for the production and collection of droplets of a first fluid, said device comprising a microfluidic platform including at least a droplet microchannel wherein is produced a flow of single droplets of said first fluid dispersed in a second fluid immiscible with the first fluid, said droplet microchannel comprising at least one inlet extremity and comprising at least one outlet extremity for the distribution of said flow of droplets.

It also relates to a method for producing and collecting droplets of a first fluid.

The device and method according to the invention are particularly useful when implemented with a first fluid comprising a plurality of particles, as it allows encapsulation of a single particle in each droplet.

TECHNOLOGICAL BACKGROUND

A microfluidic device for production of droplets of an aqueous solution containing living cells in a carrier oil with such a microfluidic platform is known from the document entitled «Droplet-based microfluidic platforms for the encapsulation and screening of mammalian cells and multicellular organisms», published by J. Clausell-Thormos et al. in Chemistry and Biology, volume 15, pages 427 to 437 in May 2008.

The use of such a microfluidic platform allows the encapsulation of single cells in microreactors formed by the aqueous droplets. This document shows that these microreactors are adapted to maintain the cells alive and even allow them to proliferate.

In this document, the flow of droplets produced in the microfluidic platform is collected as a whole, thereby forming an emulsion. This emulsion is then broken or reinjected in another microfluidic platform for analysis.

It is then impossible to collect each of the droplets separately, in order to perform further reactions if necessary.

It is also know from document WO2010/018465 to use a «droplet-in-oil» technology to encapsulate nucleic acid fragments and reagents in a droplet in order to perform a polymerase chain reaction (PCR) in the small volume of the droplets.

Thanks to the isolated environment of the droplet, the products of the reactions are protected from contamination and only a very small amount of reagents is needed.

The outcome of the PCR occurring in each droplet is optically probed while the droplets are still in the flow of droplets. Therefore, no collection of the droplets is performed in this document.

A current method for collecting single cells and studying them separately from each other is based on manual collection and deposition of these cells in the receiving areas of a microtiter plate. However, such a method is time-consuming and only allows the study of a limited number of cells.

SUMMARY OF THE INVENTION

The present invention aims at providing a device and a method for producing and collecting droplets of a first fluid in a simple, quick and economic manner, allowing the collection and study of a great number of cells.

More precisely, the invention relates to a microfluidic device as described in the introduction, comprising:
 a collection device comprising a plurality of receiving areas adapted to collect at least one of said droplets,
 means for changing the relative position of the collection device and the outlet of the microfluidic platform,
 means for controlling the flow of droplets, and
 means for synchronizing the flow of droplets at the outlet of said droplet microchannel and the relative movement of the collection device with regards to the microfluidic platform.

Thanks to this device, it is possible to deposit precisely each of the droplets exiting from the microfluidic platform in one of the receiving areas of the collection device. The droplets are then separated from each other and can be treated separately.

According to other advantageous and non limitative characteristics of the device according to the invention:
 said flow control means control at least the speed of said flow of droplets and/or the distance between two successive single droplets in said flow of droplets;
 said synchronization means synchronize the flow of droplets at the outlet extremity of said droplet microchannel and the movements of the collection device depending on the positions of the receiving areas on said collection device;
 said microfluidic platform comprises at least a first fluid microchannel fed with said first fluid and a second fluid microchannel fed with said second fluid, both of said first fluid microchannel and second fluid microchannel intersecting at the inlet extremity of said droplet microchannel and communicating with said droplet microchannel in order to merge said first and second fluid and produce said flow of single droplets of first fluid dispersed in said second fluid;
 said flow control means comprise means for controlling the pressure of said first fluid in said first fluid microchannel and means for controlling the pressure of said second fluid in said second fluid microchannel;
 said microfluidic platform comprises at least a reagent microchannel fed with a chemical or biological reagent, the reagent microchannel leading into said first fluid microchannel, upstream from the intersection between this first fluid microchannel and said second fluid microchannel;
 said flow control means comprise means for controlling the pressure of said reagent in said reagent microchannel;
 said droplet microchannel comprises a capillary with which it is fluidly connected, the end of which forms the outlet for the distribution of the flow of droplets;
 said microfluidic platform comprises probing means that allow the identification of products contained in each droplet, and preferably said probing means are located in the vicinity of the droplet microchannel;
 said probing means are connected to said synchronization means so that the identification of a droplet by its content can be coordinated with its location in the collection device;
 said device includes an electronic control unit which coordinates the actions of the flow control means, the synchronization means and possibly the probing means;
 said first fluid comprises a plurality of particles, each droplet encapsulating one or zero of these particles;
 said particles comprise at least one of the following: living or dead cells, cell organelles, organic or inorganic beads, micells, vesicles, liposomes, multicellular organisms, microorganisms;

each droplet of said flow of single droplets is produced by a transient variation of pressure of at least one of said first and second fluids in said first or second microchannel;

each droplet of said flow of single droplets is produced by a transient variation of pressure of at least said reagent in said reagent microchannel.

The invention also relates to a device for the collection and study of living cells, multicellular organisms, or microorganisms from a suspension of such cells, multicellular organisms, or microorganisms in a first fluid, wherein said device includes at least one microfluidic device as described above, and said microfluidic device is located within a controlled atmosphere enclosure.

The invention further relates to a method for producing and collecting isolated droplets of a first fluid, comprising the steps of:

a) feeding a first microchannel of a microfluidic platform with said first fluid, b) feeding a second microchannel of said microfluidic platform with a second fluid immiscible with the first fluid, c) producing, in a droplet microchannel, a controlled flow of single droplets of said first fluid dispersed in said second fluid by merging said first and second fluid at the intersection of said first fluid and second fluid microchannels with said droplet microchannel, d) distributing the flow of droplets at the outlet extremity of said droplet microchannel, e) positioning a collection device under the outlet extremity of the droplet microchannel, the collection device and the microfluidic platform being in movement relative to each other, f) synchronizing the flow of droplets arriving at said outlet of the droplet microchannel with the relative movements of the collection device.

According to another advantageous and non limitative characteristic of the method according to the invention, it further comprises the step of controlling the time elapsed between the production of a given single droplet and the arrival of this droplet at said outlet of the droplet microchannel.

The invention further relates to a method for studying and collecting particles from a suspension of said particles in a first fluid, comprising the steps of:

producing isolated droplets of said first fluid in a microfluidic device, the dilution of the first fluid being controlled so that each droplet encloses a controlled number of particles, and collecting the droplets in a collection device, said steps being performed according to the method described above.

According to other advantageous and non limitative characteristics of this method:

it further comprises the step of introducing a reagent into said first fluid microchannel, upstream from the intersection between this first fluid microchannel and said second fluid microchannel;

it further comprises the step of controlling the time elapsed between:

the moment when a particle is put in contact with the reagent by introduction of said reagent in said first fluid microchannel, and the formation of a droplet comprising said particle by merging of said first and second fluid;

said particles are cells and said reagent comprises a cell lysis agent and/or a reverse transcriptase enzyme.

The devices and methods of the invention allow the automated production of droplets containing a controlled number of particles from a suspension of such particles in a fluid. It allows their collection in reception means wherein they are located in individual receiving areas, and the attribution of a precise receiving area to a particle as a function of its identification through probing means. The methods and devices of the invention allow the performing of reactions on particles contained within these droplets with a precise timing between the introduction of these particles in the microfluidic device and their distribution into the reception means.

BRIEF DESCRIPTION OF THE DRAWINGS

A more complete appreciation of the invention and many of the advantages thereof will be readily obtained as it becomes better understood by reference to the detailed description when considered in connection with the accompanying drawings, wherein:

FIG. 1 is a schematic view of the device according to an embodiment of the invention, and FIG. 2 is a detailed view of the area A of FIG. 1.

DETAILED DESCRIPTION OF EMBODIMENTS OF THE INVENTION

FIG. 1 shows a microfluidic device 100 for production and collection of droplets 14 of a first fluid 11.

This microfluidic device 100 comprises a microfluidic platform 110.

This microfluidic platform 110 comprises a support 111 wherein a network of microchannels 116A, 116B, 117, 118, 119 is formed. These microchannels typically exhibit a section inferior to 16000 micrometers square.

According to a known method of fabrication of the support 111 of the microfluidic platform 110, it is fabricated by patterning halves of microchannels exhibiting a depth typically in the range of 40 to 700 micrometers into the sides of two blocks of polymer, for example polydimethylsiloxane, also called PDMS, by using a technique of soft lithography.

In order to achieve this step, the polymer is poured over a mold made of a light-sensitive resin such as SU-8. The SU-8 mold is typically obtained by photolithography. The two blocks are then aligned in order to place the halves of the microchannels in front of each other and bound together in order to form the microchannels. The width and depth of the microchannels thus obtained are for example in the range between 50 and 300 micrometers.

According to a variant, the polymer block obtained comprising the microchannels can be bound to a glass slide to be less flexible. The side of the polymer block opposite to the glass slide is called the front face of the microfluidic platform 110.

Alternatively, another polymer known as Dyneon™ THV and commercialized by 3M may be used to achieve the support of the microfluidic platform, thanks to another technique known as "hot embossing". Using this technique, the two halves of the support each containing halves of the microchannels may be fabricated, for example out of Dyneon™ THV 500, and bound together by a thin layer of Dyneon™ THV 221. The dimensions of the support and microchannels are equal to those described before.

The "hot embossing" technique and bounding of the two halves are described in more details in the paper titled "New family of fluorinated polymer chips for droplet and organic solvent microfluidics", by authors Begolo et al., published in Lab on a chip, issue 3, 2011, pages 508-511, by The Royal Society of Chemistry.

The inlet hole of each microchannel is punctured through the polymer block in order to fluidly connect the microchannels to the front face of the microfluidic platform 110.

More precisely, the microfluidic platform 100 comprises at least a first fluid microchannel 117 fed through a first fluid inlet hole 114 with said first fluid 11, a second fluid microchannel 116A, 116B fed through a second fluid inlet hole 113 with a second fluid 10 immiscible with said first fluid 11, and a droplet microchannel 119 wherein droplets 14 of the first fluid 11 are dispersed in the second fluid 10.

In the example described below, said first fluid 11 is an aqueous suspension of cells 12 and the second fluid 10 is a carrier oil.

The suspension of cells 12 is fed through the first fluid hole 114 thanks to a cone or tube introduced into the first fluid inlet hole 114.

Here, the microfluidic platform 110 comprises at least an external pressure-actuated valve V1 and the suspension of cells is fed through the first fluid hole 114 thanks to a tube 141 fluidly connecting the first fluid microchannel 117 to this pressure-actuated valve V1.

This pressure-actuated valve V1 is made of an arrangement of microchannels patterned into a block of polymer obtained in a similar fashion as described before. It consists of a pressure-actuated microchannel located above another microchannel, called thereafter inlet microchannel. The inlet microchannel has an inlet hole fluidly connected to a first fluid reservoir and an outlet hole fluidly connected to the tube 141. This tube 141 is then fluidly connected to the inlet hole 114 of the first fluid microchannel 117.

The first fluid pressure in the inlet microchannel may be controlled through a commercially available pressure controller.

The pressure-actuated microchannel is only separated from the inlet microchannel by a thin membrane of polymer. A pressure fluid is injected into said pressure-actuated microchannel with a pressure controlled by first fluid flow control means 140.

The first fluid flow control means 140 comprise for example solenoid valves actuated with an air pressure of 1 bar and controlled by a dedicated software. When the pressure fluid is injected with a pressure below a given threshold value, the membrane is not deflected and the first fluid 11 flows continuously through said inlet microchannel, and subsequently through said first fluid microchannel 117, whereas when this pressure is superior to the threshold value, the membrane is deflected and blocks the flow of first fluid 11 through the inlet microchannel, and subsequently through said first fluid microchannel 117.

The pressure fluid used is for example water.

The inlet microchannel and the pressure-actuated microchannel may either follow aligned or orthogonal routes.

Alternatively, the pressure-actuated valve V1 may be located on the path of the first fluid microchannel, downstream from the first fluid inlet hole.

The carrier oil is pushed continuously in a controlled manner through the second fluid inlet hole 113 thanks to an injection device 160 comprising a syringe or a tank placed above the microfluidic platform 110 and feeding the second fluid microchannel under the effect of gravity. The injection device 160 comprises a commercially available pressure control device to control the pressure of the injected oil.

The cell suspension 11 and the oil 10 are typically injected in the microfluidic platform 110 with a pressure in the range of 0 to 1 bar.

The first fluid flow control means 140 and oil injection means 160 are computer controlled by an electronic control unit 180 (FIG. 1), as will be described in more details below.

Said first fluid microchannel 117 and second fluid microchannel 116A, 116B intersect at an inlet extremity of said droplet microchannel 119 and communicate with this droplet microchannel 119 in order to merge said first 11 and second fluid 10 and produce said flow of single droplets 14 of first fluid 11 dispersed in said second fluid 10.

The droplet microchannel 119 comprises here one inlet extremity located at the intersection I of said first fluid and second fluid microchannels 11. It also comprises a capillary 170 to which it is fluidly connected. The free end of this capillary 170 forms an outlet 171 for the distribution of the flow of droplets 14.

In practice, the droplet microchannel 119 opens up to the front face of the polymer block forming the support of the microfluidic platform 110 in an enlarged pear-shaped opening. The capillary 170 is introduced into this opening and glued to the microfluidic platform 110. A photocurable glue can for example be used for this purpose. A droplet of glue is introduced between the capillary and the platform by capillarity and cured by illumination with ultra-violet light. Other types of glue may also be used, that does not require ultra-violet light to be cured, such as cyanoacrylate glue for example.

Other microchannels may be used to add any kind of component to said first fluid 11 and second fluid 10.

In the example shown on FIG. 1, the microfluidic platform 110 comprises at least an additional microchannel 118 fed at a third fluid inlet hole 115 with a third fluid 13 miscible with said first fluid 11.

This third fluid 13 is for example a chemical or biological reagent adapted to react with the cells 12 in suspension in the first fluid 11.

This additional microchannel 118 leads into said first fluid microchannel 117, upstream from the intersection between this first fluid microchannel 117 and said second fluid microchannel 116A, 116B or said droplet microchannel 119.

The introduction of said reagent into the first fluid 11 may be controlled by a pressure-actuated valve V2 similar to the pressure-actuated valve V1 described in conjunction with the introduction of the first fluid 11, and similarly controlled through reagent flow control means 150 by the electronic control unit 180. The third fluid inlet hole 115 is then fluidly connected to the corresponding pressure-actuated valve V2 via a tube 151, as shown on FIG. 1.

Different paths may be considered for the microchannels of the microfluidic platform 110.

In the example shown on FIG. 1, all microchannels intersect at the same location I, shown in an enlarged view on FIG. 2.

More precisely, the route followed by the second fluid microchannel 116A, 116B has a rectangular shape, with its inlet hole 113 located on the middle of one of the sides of this rectangle. The flow of second fluid 10 injected through said second fluid inlet hole 113 is thus divided into two streams flowing in opposite directions from the inlet hole 113. These two streams then flow parallel in two opposite sides of the rectangle formed by said second fluid microchannel 116A, 116B and are reunited at the location I of the intersection of all microchannels.

This intersection I is thus located opposite to the second fluid inlet hole 113 on the rectangle second fluid microchannel 116A, 116B.

Said first fluid microchannel 117 and additional microchannel 118 form a V-shape pointing at the intersection I, on one side of the second fluid microchannel 116A, 116B.

The droplet microchannel 119 extends from this intersection point, perpendicularly to the second fluid microchannel 116A, 116B, away from said first fluid microchannel 117.

In this configuration, said first and third fluids are then mixed together immediately before the production of the droplet 14.

The droplet 14 is formed as shown on FIG. 2 by squeezing the flow of first fluid 11 mixed with said third fluid 13 by the opposite flows of second fluid 10 in the second fluid microchannel 116A, 116B (FIG. 2). The formation of the droplet occurs whenever the pressure-actuated valve V1 controlling the flow of first fluid is opened. The flows of first, second and third fluids through corresponding microchannels are indicated on FIGS. 1 and 2 by arrows.

The carrier oil may comprise a surfactant in order to favor the formation of the droplets 14. In the example described here, no surfactant is added, as the reagent used already comprises components adapted to stabilize the droplets.

In a variant, the additional microchannel intersects the first fluid microchannel upstream from said intersection I with the second fluid microchannel. The time elapsed between mixing said first and third fluids and producing the droplets is thus increased.

In another variant (not shown), said first fluid microchannel, second fluid microchannel and droplet microchannel exhibit a T-shape geometry. The first fluid and second fluid microchannels intersect at right angle and the droplet microchannel extends from the intersection, in the continuity of said second fluid microchannel.

Any kind of known arrangement of microchannels adapted to produce droplets of a first fluid in a second fluid may be used.

The droplets 14 of aqueous solution in oil formed in the droplet microchannel 119 represented on FIG. 2 exhibit here an elongated shape. Their width W is approximately equal to the width of the droplet microchannel 119. Their length L is equal to one to three times their width. The volume of these droplets is between 2 and 20 nanoliters.

In order to ensure a regular flow of droplets 14 in said droplet microchannel 119 and in said capillary 170 to the outlet 171 of the microfluidic platform 110, the inner face of the droplet microchannel 119 and of the capillary 170 preferably exhibit hydrophobic properties. They may be formed in a hydrophobic material or coated with a hydrophobic coating.

PDMS is particularly well suited as it is a hydrophobic material. Glass or other polymers may also be used.

Moreover, the capillary inner section is preferably about the same as the droplet microchannel 119 inner section.

Depending on the first fluid 11 concentration in cells 12, one or more cell 12 may be encapsulated in the droplets 14 produced in the droplet microchannel 119, as shown on FIG. 2.

More precisely, the number of cells encapsulated in each droplet 14 is statistical and follows a distribution of Poisson, as was shown for example in the previously cited document «Droplet-based microfluidic platforms for the encapsulation and screening of mammalian cells and multicellular organisms», published by J. Clausell-Thormos et al. in Chemistry and Biology, volume 15, pages 427 to 437 in May 2008.

It is therefore possible, by decreasing the concentration of cells 12 in the first fluid 11, to encapsulate zero or one cell 12 in each droplet 14, meaning that the probability of encapsulating two or more cells in a droplet can be greatly limited.

In other words, varying the concentration of cells 12 in the suspension allows controlling the statistical distribution of the number of cells trapped in each droplet 14.

The concentration of cells in the first fluid can either be predetermined in the suspension introduced in the first fluid inlet hole 114, or controlled on site, by diluting a suspension exhibiting a high concentration of cells when introduced in the microfluidic platform with an aqueous solution introduced in the first fluid microchannel through an additional microchannel as described before.

The concentration of cells in the first fluid 11 can then be computer-controlled.

The number of cells encapsulated in each droplet 14 may be probed thanks to probing means 200 while they are still flowing in the droplet microchannel 119.

These probing means 200 are for example phase contrast microscopy means or fluorescence measuring means. In this later case, the membrane or cytoplasm of the cell has to be marked with fluorophores.

The probing means 200 may also comprise other types of analysis means such as absorbance measurements or conductance measurements means.

In a remarkable fashion, said microfluidic device 100 also comprises:
- a collection device 120 for collecting said droplets,
- means 130, 181 for changing the relative position of the collection device 120 and the outlet 171 of the microfluidic platform 110,
- means 140, 150, 160, 182 for controlling the flow of droplets 14, and
- means 183 for synchronizing the flow of droplets 14 at the outlet 171 of said microfluidic platform 110 and a relative movement of the collection device with regards to the microfluidic platform 110.

The collection device 120 comprises a plurality of receiving areas 122 adapted to collect at least one of said droplets 14.

In the example shown on FIG. 1, this collection device 120 is a microtiter plate 120. It comprises a support 121 in the form of a flat plate with a plurality of wells 122 opened to a front face 123 of the support 121. This support 121 is typically made of rigid or flexible plastic material.

The microtiter plate 120 typically has 6, 12, 24, 96, 384 or 1536 wells 122 arranged in a rectangular matrix. The wells 122 can either exhibit a circular or square section.

Each well 122 of the microtiter plate 120 is adapted to hold between tens of nanoliters to several milliliters of liquid.

The front face 123 of the microtiter plate 120 is oriented toward the outlet 171 of the microfluidic device 110, in order to allow the droplets exiting from this outlet 170 to fall under the action of the gravity into the wells 122 of the microtiter plate 120.

The schematic view of FIG. 1 shows a simplified relative arrangement of the microfluidic platform 110 and the microtiter plate 120, where the capillary 170 extends straight from the microfluidic platform 110.

However, the capillary 170 is advantageously flexible, and allows to bring the droplets in front of the wells 122 of the microtiter plate 120 while the microfluidic platform 110 lays for example in a plane parallel to the microtiter plate 120.

This capillary 170 is made for example of flexible plastic material, such as polytetrafluoroethylene (PTFE).

In the example shown schematically on FIG. 1, these wells 122 are filled with oil prior to the droplet deposition. The droplets fall into the well, under the oil phase, then remain isolated from air and from their environment, and thereby are protected from contamination or evaporation.

In practice, each droplet remains surrounded by a film of oil when exiting the capillary 170.

Moreover, in a preferred embodiment of the method according to the invention, the outlet 171 of the capillary 170 is brought to or under the surface of the oil contained in each well 122, so that the droplet 14 exiting the capillary 170 avoids any contact with air.

In the example shown on FIG. 1, the means 130, 181 for changing the relative position of the collection device 120 and the outlet 170 of the microfluidic platform 110 comprise translation means 130 of the microtiter plate 120.

The outlet 170 of the microfluidic device 110 thus remains fixed, while the microtiter plate 120 is moved along two perpendicular axis X, Y in the plane of the microtiter plate 120. Each well 122 can thus be brought successively in front of the outlet 171 of droplet microchannel 119.

The direction and amplitude of the translation movement imposed to the microtiter plate 120 by the translation means 130 are computer-controlled by translation control means 181 of the electronic command unit 180 as will be described in more details later on.

In order to allow the precise deposition of a droplet 14 in each of the wells 122 of the microtiter plate 120, the microfluidic device 100 also comprises means 182 for controlling the flow of droplets 14.

These flow control means 182 are implemented by the electronic control unit 180 that controls the oil injections means 160 of the oil carrier and the first fluid flow and reagent flow control means 140, 150.

The control of the oil injection means 160 allows to regulate the flow rate of oil 10 through the second-fluid microchannel 116A, 116B and thus to adjust the speed of the oil carrier flow. The speed of said flow of droplets 14 is thus controlled.

The control of the first fluid flow control means 140 allows to regulate the frequency of opening and closing of the inlet microchannel of the valve V1 and subsequently of first fluid microchannel 117.

This frequency determines the frequency at which the droplets of first fluid 11 are produced, and thus regulates the distance between two successive single droplets 14 in said flow of droplets for a given flow rate of oil 10.

The reagent flow control means 150 are synchronized with the first fluid flow control means 140, in order to mix the reagent and suspension just before production of each droplet.

Finally, the electronic control unit 180 implements the synchronization means 183. These synchronization means 183 synchronize the flow of droplet 14 at the outlet 171 of said microfluidic platform 110 and the movements of the collection device 120 by controlling the droplet flow control means 182 and the translation control means 181 depending on the positions of the receiving areas 122 on said collection device 120.

More precisely, in the example described here, these synchronization means 183 ensure that, during the time between the reception of a first droplet 14 in a first well 122 of the microtiter plate 120 and the reception of a second droplet 14, the microtiter plate 120 is moved from a position where the outlet 171 of the microfluidic platform 110 faces said first well 122 to a position where the outlet 171 faces a second well 122 distinct from the first well 122.

In a preferred embodiment of the invention, a single droplet is deposited in each of the wells of the microtiter plate 120. However, one can consider depositing a plurality of droplets into given wells or no droplet in some other wells.

The synchronization means 183 also allow the identification of the droplet deposited in each well 122.

More precisely, the conditions of production of the droplet 14, namely, introduction of reagent, nature of the reagent if several additional microchannels are connected to the first fluid microchannel 117, concentrations of these reagents if these are varied in time, concentration of cells in the suspension in the case where this concentration is adjusted on site, can be recorded by the electronic control unit 180 and associated with the position of the well where the corresponding droplet was deposited.

The result of the analysis by the probing means 200 for each droplet 14 can also be recorded by the electronic control unit 180 and associated with the position of the corresponding well 122.

In a variant, the first fluid comprises a suspension of particles comprising at least one of the following: living or dead cells, cell organelles such as mitochondria, organic or inorganic beads, for example beads of polymer, micells, vesicles, liposomes, multicellular organism, microorganisms such as bacteria.

In these cases, the droplets produced encapsulate a controlled number of particles.

In the case where the microfluidic device is used for collecting and studying cells, multicellular organisms, or microorganisms, the microfluidic device 100 is preferably located within a controlled atmosphere enclosure, which provides controlled conditions such as pressure, humidity and temperature, permitting cell survival, and minimizes the risks of contamination.

In practice, the microfluidic device 100 is particularly useful when used to analyze the transcriptome of each of the cells initially contained in the suspension fed to the first fluid microchannel of the microfluidic platform 110.

The following steps are therefore implemented by the electronic control unit 180 to produce and collect isolated droplets of said cell suspension while performing at the same time cell lysis and mRNA reverse transcription of the messenger ribonucleic acids, called mRNA of the corresponding cell.

The electronic control unit 180 controls the feed of the cell suspension 11 to said first fluid microchannel 117 of said microfluidic platform 110 and the feed of said reagent microchannel 118 with a mix of cell lysis inducing agent and reverse transcriptase enzymes.

The reagents are mixed with the cell suspension at the intersection I of the microchannels, just before or during formation of the droplets. More precisely, in a preferred embodiment, the reagents are mixed with the cell suspension between 0 and 1 second before formation of the droplets.

The lysis of the cell is then performed within a few seconds, while the corresponding droplet is produced and carried away in the system.

The electronic control unit 180 controls the feed of the second fluid microchannel 116A, 116B of said microfluidic platform 110 with said carrier oil 10 and the production, in the droplet microchannel 119, of a controlled flow of single droplets 14 of said mix between the cell suspension and the reagent, dispersed in the carrier oil, as described before.

The droplets here contain preferably either only the reagent, in the case no cell was encapsulated, or a solution containing the mRNA of a single cell.

If a cell was encapsulated, the reverse transcriptase enzymes perform the retrotranscription of the mRNA of the cell while the droplet produced flows along the droplet microchannel 119.

In order to help the retrotranscription being performed, the carrier oil may be heated at 42 degrees Celsius, that is to say, the temperature at which the reverse transcriptase enzymes are most efficient.

The probing means 200 may here comprise optical analysis means to determine which droplets contain biological material with mRNA and which droplets comprise only the reagents. In this way, the wells 122 of the microtiter plate 120 that will be empty from molecules of interest may be easily identified and thrown away.

The flow of droplets 14 is then distributed at the outlet 171 of said microfluidic platform 110.

The electronic control device 180 controls the positioning of the microtiter plate 120 under the outlet 171, and synchronizes the flow of droplets 14 arriving at said outlet 171 with the relative movements of the microtiter plate 120 in order to deposit one droplet 14 in each well 122.

Advantageously, the time elapsed between the production of a given single droplet 14 and the arrival of this droplet 14 at said outlet 171 of the microfluidic plate 110 can be controlled by the electronic control unit 180.

The electronic control unit 180 therefore adjusts the flow rate of the carrier oil in the droplet microchannel 119. A lower flow rate will slow the progression of the droplets 14 in the droplet microchannel 119 and therefore increase the time spent by the droplets in the microfluidic platform 110.

Here only a few seconds is preferably elapsed between the production of the droplet and its deposition into the microtiter plate 120.

The risks of damaging the mRNA of the cell, and therefore the risks of losing part of the information comprised in the transcriptome of the cell are thus decreased.

In the context of the analysis presented above, it was preferred to mix reagents and cell suspension at the time of production of the droplets in order to avoid lysis of the cell before encapsulation. The applicant demonstrated that it needs at least 1 to 2 seconds for a cell to be in contact with the reagents before lysis initiates.

However, other reactions may require a longer time between mixing the reagents and particles of the first fluid and producing the droplets.

In this case, the microfluidic device used comprises a reagent microchannel that intersects the first fluid microchannel upstream from the intersection with the second fluid channel.

In this way, the electronic control unit may control the time elapsed between the moment when a particle is put in contact with the reagent by introduction of said reagent in said first fluid microchannel, and the formation of a droplet comprising said particle by merging of said first and second fluid, by controlling the flow rate of first fluid in the first fluid microchannel. This flow rate is related to the frequency of activation of the corresponding first fluid flow control valve.

Thanks to the invention, each droplet 14 containing the transcriptome of a single cell 12 of the initial sample suspension in the first fluid is collected individually in one of the wells 122 of the microtiter plate 120. They can therefore be subsequently treated, for example for amplification of the genetic material by polymerase chain reaction.

Although the present invention has been described in details with respect to certain embodiments and examples, variations and modifications exist which are within the scope of the present invention as defined in the following claims.

For example, the means for controlling the flow of droplets comprise here an external pressure-actuated valve that opens or closes the first fluid microchannel.

Advantageously, the control of the pressure of at least one of said first, second or third fluid in the corresponding microchannel of the microfluidic device may also be used to generate droplets in a controlled manner without restricting the flow path of any of these first, second and third fluids.

In this case, no pressure-actuated valve needs to be used. First and third fluids are simply loaded in small reservoirs or vials, each of them being fluidly connected to the corresponding inlet in the microfluidic device and linked to the pressure control means. The second fluid is for example injected through injection means similar to those described above.

The gas pressure applied on top of said reservoir or vial containing said first or third fluid to introduce this fluid into the microfluidic device is then dynamically controlled to produce the transient pressure variation in the fluid flowing in the corresponding microchannel. The injection means of the second fluid may also be used to produce such a pressure variation in the second fluid.

In such a variant, the production of a droplet may then be triggered by a transient negative variation of pressure of said second fluid in the second microchannel of the microfluidic device.

In another such variant, the production of a droplet may be triggered by a transient positive variation of pressure of said first fluid and said third fluid, or of said second fluid, in the corresponding microchannels of the microfluidic device.

This avoids the use of valves, which are complicated to fabricate and may raise reproducibility and time constant problems.

Transient positive or negative variations of pressure are for example achieved through a square variation of pressure of the corresponding fluid in time.

Alternatively, the production of the droplets may be controlled by electric, thermal or acoustic means.

The electric control means may comprise electrodes producing an electric field in the vicinity of the intersection between first fluid and second fluid microchannels. The first fluid comprising a dielectric aqueous solution, when activated, the electric field may exert a force on the first fluid, thereby accelerating it and producing a droplet.

The thermal control means may comprise heating means in the vicinity of the intersection between first fluid and second fluid microchannels. When these heating means heat the oil, the oil expands, thereby blocking the production of a droplet. When the oil cools down, it shrinks and allows the production of a droplet.

The acoustic control means comprise means for producing an acoustic wave that induces a pressure variation in the first fluid, thereby favoring the production of a droplet.

Other collection means may be used, such as a glass plate with a coating comprising hydrophilic zones forming the reception areas and being surrounded by hydrophobic zones.

The microfluidic platform described here is meant to be disposable, but reusable platform may be achieved in a similar fashion.

Materials and Methods

First Example

Microfluidic Platform Fabrication

Single-use microfluidic devices were fabricated by soft-lithography. PDMS microfluidic platforms were made using replica molding of a SU8-mold patterned by ultraviolet-lithography.

The height and the width of the channels were 125 micrometers except at the pear-shaped junction hole with the capillary of the droplet microchannel where they were 500 micrometers and 700 micrometers respectively.

The channels were formed by adjusting two PDMS parts, each comprising the imprint of half of the microchannels.

A thick layer (about 7 millimeters) of PDMS was produced by pouring a 10:1 mixture of a monomer (GE RTV 615 component A) and a hardener (GE RTV 615 component B) onto a first mold placed in a Petri dish and left at room temperature for 15 minutes to degas.

A thin layer (about 3 millimeters) of PDMS was produced by pouring a 10:1 mixture of a monomer (GE RTV 615 component A) and a hardener (GE RTV 615 component B) onto a second mold placed in a Petri dish and left at room temperature for 15 minutes to degas.

The first and second molds are adapted to imprint half of the microchannels.

The two layers were heated for 45 minutes at 78 degrees Celsius.

Inlet holes for the injection of first and second fluids were punched on the first PDMS part.

The two PDMS parts were bound together with a dioxygen plasma cleaner and aligned.

The device was left for a week at 78 degrees Celsius.

A polyether ether ketone tube, also called PEEK tube, from Upchurch, with an outer diameter of 510 micrometers and an inner diameter of 125 micrometers was introduced at the pear-shaped junction hole.

Then a ultraviolet-curable glue (NOA 81®, Norland Optical Adhesive) was deposited between the PEEK tube and the PDMS and cured by a uniform illumination at 365 nanometers wavelength with a Hamamatsu LC8 lamp.

Pressure-Actuated Valves Fabrication

Single-use microfluidic valves were fabricated by multi-layer soft-lithography. Valve parts were made by replica molding of a SU8-mold and a positive resist mold (Ma-P 1275 HV) patterned by ultraviolet-lithography.

Each pressure-actuated valve consisted of two levels of microchannels. The first fluid or reagent circulates in the bottom layer comprising fluidic channels, while the top channels, called control channels, operate the pressure-actuated valves.

The typical dimensions used for the valves were 40 micrometers for the height and 500 micrometers for the width of the first fluid or reagent parabolic-shaped channel and 80 micrometers for the height and 500 micrometers for the width of the rectangular control channel.

A thick layer of PDMS was produced by pouring a 5:1 mixture of a monomer (GE RTV 615 component A) and a hardener (GE RTV 615 component B) onto the mold placed in a Petri dish and left at room temperature for 15 minutes to degas. PDMS (20:1 mixture) was spin-coated at 90° rotations per minute for 60 seconds onto the mold for making the associated control channels.

The two layers were cured for 45 minutes at 78 degrees Celsius. Holes for the control channels were punched.

The layers of the first fluid or reagent channel were aligned to those of the control channel. The two layers device was cured overnight. Holes for first fluid or reagent channels were then punched. The device was eventually sealed onto a pre-cleaned glass slide after a 40 seconds plasma treatment and left overnight at 78 degrees Celsius.

Molds Fabrication

The resist molds used for PDMS casting were obtained using ultraviolet optical lithography. The optical masks were designed using the layout editor CleWin and were printed on transparencies using a high-resolution printer.

The first mold was made of SU8-2100 photoresist in two steps using the MicroChem® protocol for 120 micrometers high channels for the first mask and 90 micrometers high channels for the second mask.

The second mold was made of SU8-3050 photoresist in two steps using the MicroChem® protocol for 50 micrometers high channels for the first mask and 90 micrometers high channels for the second mask.

The molds corresponding to the valve control channels were fabricated by optical lithography in an 80 micrometers thick layer of SU8 3050 photoresist (MicroChem®).

The mold corresponding to the fluidic channels was fabricated in a 40 micrometers thick layer of Ma-P 1275 HV photoresist (Microresist technology) and rounded at 150 degrees Celsius for 15 minutes.

Microtiter Plate Preparation

A microtiter plate from FrameStar 4titude was modified.

A ultraviolet-curable glue (NOA 81® from Norland Optical Adhesive) was deposited in the holes of the plate and cured by a uniform illumination at 365 nanometers wavelength using a Hamamatsu LC8 Lamp, in order to fill any gap that may be present within the wells and make them oiltight.

The microtiter plate was placed on a Märzhauser translation stage. The translation was controlled by Labview via a Tango Desktop Controller.

Each well of the plate was then filled with M5904 mineral oil from Sigma.

Device Operation

Cell suspension, reagents and oil injections were controlled by a commercially available pressure controller MFCS 8C from Fluigent. Oil was injected in the microfluidic platform oil inlet. Cell suspension and reagents were injected via the pressure-actuated valves.

The oil was M5904 Mineral Oil from Sigma.

The reagent for reverse transcription was composed of 2× first strand synthesis buffer, 2 millimoles per liter of dNTPs mix, 0.5 milligramme per milliliter of BSA (Bovine Serum Albumin) from Sigma Aldrich, 20 unities of Rnase inhibitor (Promega), 2 micromoles per liter of 3'SMART CDS primer (5'AAGCAGTGGTATCAACGCAGAGTACT30VN-3') (SEQ ID NO: 1), 2 micromoles per liter of template switching primer (5'AAGCAGTGGTATCAACGCAGAG-TACGCGGG-3') (SEQ ID NO: 2) and 3 microliters Verso enzyme mix (Thermoscientific).

The cells were suspended in Phosphate Buffered Saline.

In order to reduce first fluid and reagent consumption, they were first loaded in a 10 microliters pipette tip before being injected in the inlet of the first fluid or reagent microchannels in the corresponding pressure-actuated valve.

The outlet of the first fluid or reagent microchannel of each valve was connected to the corresponding inlet hole in the microfluidic platform with a PEEK tube.

The pressure-actuated valves were used to stop the flow or actuate the droplets generation by alternatively opening and closing the first fluid microchannel.

The control channels of the valves were filled with water and connected to a purpose-built controller based on solenoid valves such as LHDA 12VDC from Lee Corp. Typically, air pressures of 1 bar were used to actuate each valve. Digital signals sent to the solenoid valves were stored on a digital I/O card (NI PCI-6534, National Instruments) controlled with Labview.

The device was placed under a microscope so that the flow-focusing junction could be observed, and the output PEEK tube was fixed just below the oil surface and above the center of the first well of the microtiter plate.

A Labview script allowed to control the flow of droplets and to synchronize the stage displacement with the frequency of generation of the droplets determined by the frequency of opening and closing of the pressure-actuated valves.

Once the generation of droplets was regular and controlled by the valves, the Labview program ordered the translation of the stage according to a predefined map, so that each well of the microtiter plate passed and stopped below the output PEEK tube and collected a droplet. The whole plate was travelled step by step.

PCR Amplification of the Droplets

Then the microtiter plate was placed in a thermocycler at 42 degrees Celsius for 30 minutes.

Part of the mineral oil was aspirated and 50 microliter of TS-PCR mixture was added in each well. The microtiter plate was centrifuged for 1 minute at 1000 rotations per minute and placed on a thermocycler for PCR amplification. The 50 microliters of TS-PCR mix contained 1.25 micromoles per liter of 5'PCR primer (AAGCAGTGGTAT-CAACGCAGAGT) (SEQ ID NO: 3), 500 micromoles per liter of dNTPs mix, 1× Extensor Hi-Fidelity Buffer 1 and 2.5 unities of Extensor Hi-Fidelity PCR enzyme mix (Thermoscientific).

PCR amplification cycles were the following: 95 degrees Celsius for 1 minute then 35 cycles of 95 degrees Celsius for 15 seconds, 65 degrees Celsius for 30 seconds and 68 degrees Celsius for 6 minutes. Amplified cDNAs were purified using the NucleoSpin® Extract II (Macherey-Nagel) and labelled with 20 micromoles per liter of dUTP-Cy3 (GE Healthcare) and 100 millimoles per liter of random hexamers (GE Healthcare) in the presence of 50 unities of Klenow fragment (Ozyme). The reaction was performed overnight at 37 degrees Celsius.

Second Example

Microfluidic Platform Fabrication

Single-use microfluidic devices were fabricated by hot embossing.

PDMS microfluidic masters were made using replica molding of an aluminium mold patterned by micromachining.

The height and the width of the channels were 125 micrometers except at the output of the chip where they were 500 micrometers and 700 micrometers respectively with the shape of a cross.

A thick layer (about 7 millimeters) of PDMS was produced by pouring a 10:1 mixture of a monomer (GE RTV 615 component A) and a hardener (GE RTV 615 component B) onto the first mold placed in a Petri dish and left at room temperature for 15 min to degas.

A thick layer (about 3 mm) of PDMS was produced by pouring a 10:1 mixture of a monomer (GE RTV 615 component A) and a hardener (GE RTV 615 component B) onto the second mold placed in a Petri dish and left at room temperature for 15 min to degas.

The two PDMS molds were heated for 45 minutes at 78 degrees Celsius.

THV 500 pellets (Dyneon™ THV 500G, 3M, USA) were first cleaned by sonication in water and ethanol for 30 minutes and then dried at 100 degrees Celsius for 1 hour.

THV 500 pellets were then moved onto the PDMS molds and melted at 200 degrees Celsius overnight. This step was done in a vacuum oven (Fisher Bioblock).

Then the THV 500 replica were peeled off from the PDMS master.

Holes for the injection sites were punched on the first THV 500 part.

A silicon wafer was used as a substrate for spin coating a thin layer of THV 221 (Dyneon™ THV 221, 3M) using a saturated solution of polymer in acetone. The first THV 500 part was then placed in contact with the thin THV 221 layer for 2 minutes in a heated hydraulic press (Specac) at 120 degrees Celsius and with a pressure of approximately 1 MegaPascal (MPa). This part was peeled off.

The channels were formed by adjusting the two THV 500 parts.

The two THV 500 parts were aligned and bound together under pressure at 110 degrees Celsius by applying a controlled pressure (2 MPa) at 120 degrees Celsius for 1 hour.

A PEEK tube (Upchurch 510 µm OD×ID 125 µl) was introduced at the output of the system. Then a UV-curable glue (NOA 81, Norland) was deposited between the PEEK tube and the PDMS and cured by a uniform 365 nm illumination (LC8 Lamp Hamamatsu).

Molds Fabrication and Microtiter Plate Preparation

The aluminum molds used for PDMS casting were obtained using micromachining. The surface was polished and channels were dug, for example thanks to a drill.

Device Operation

Cell suspension, reagents and oil injections were controlled by a commercially available pressure controller MFCS 8C from Fluigent.

Oil was injected in the microfluidic platform oil inlet via a PEEK tube connected to a Fluiwell tank from Fluigent.

In order to reduce first fluid and reagent consumption, they were first loaded in a 10 microliters pipette tip before being injected in the inlet of the first fluid or reagent microchannels through the corresponding entrance.

The oil was M5904 Mineral Oil from Sigma.

The reagent for reverse transcription was composed of 2× first strand synthesis buffer, 2 millimoles per liter of dNTPs mix, 0.5 milligramme per milliliter of BSA (Bovine Serum Albumin) from Sigma Aldrich, 20 unities of Rnase inhibitor (Promega), 2 micromoles per liter of 3'SMART CDS primer (5'AAGCAGTGGTATCAACGCAGAGTACT30VN-3') (SEQ ID NO: 1), 2 micromoles per liter of template switching primer (5'AAGCAGTGGTATCAACGCAGAG-TACGCGGG-3') (SEQ ID NO: 2) and 3 microliters Verso enzyme mix (Thermoscientific).

The cells were Human Embryonic Kidney cells diluted at 100 cells per microliter in Phosphate Buffered Saline.

The control of the oil injection means was used to produce droplets through square variations of pressure of the oil.

The device was placed under a microscope so that the flow-focusing junction could be observed, and the output PEEK tube was fixed just below the oil surface and above the center of the first well of the microtiter plate.

A Labview script allowed to control the flow of droplets and to synchronize the stage displacement with the frequency of generation of the droplets determined by the frequency of the square variations in oil pressure.

Once the generation of droplets was regular, the Labview program ordered the translation of the stage according to a predefined map, so that each well of the microtiter plate passed and stopped below the output PEEK tube and collected a droplet. The whole plate was travelled step by step.

PCR Amplification of the Droplets

This step was performed as described in the first example.

Electrophoresis analysis of the mixture contained in each well after the PCR step showed that the transcriptome of individual cells were indeed amplified through PCR.

The invention claimed is:

1. Microfluidic device for the production and collection of droplets of a first fluid, said device comprising:
   a microfluidic platform comprising:
      a first fluid microchannel fed with said first fluid, and a first fluid inlet in fluid communication with the first fluid microchannel;
      a second fluid microchannel fed with a second fluid immiscible with said first fluid, and a second fluid inlet in fluid communication with the second fluid microchannel, wherein the second fluid microchannel splits into two fluid microchannels, and then said two fluid microchannels converge and intersect with the first fluid microchannel; and
      a droplet microchannel,
      said first fluid microchannel and second fluid microchannel intersecting at an inlet extremity of said droplet microchannel and communicating with said droplet microchannel in order to merge said first and second fluids, wherein is produced within said droplet microchannel of the microfluidic platform a flow of single droplets of said first fluid dispersed in said second fluid immiscible with the first fluid,
      said droplet microchannel also comprising an outlet extremity for the distribution of said flow of droplets exiting the droplet microchannel,
   a collection device positioned separate and outside of the microfluidic platform, comprising a plurality of receiving areas adapted to collect at least one of said droplets exiting the droplet microchannel through the outlet extremity,
   means for moving the collection device and all of its plurality of receiving areas and the outlet of the microfluidic platform relative to each other, in order to place said outlet in front of one of said plurality of receiving areas,
   means for controlling the flow of droplets by controlling the time elapsed between the production of a given single droplet and the arrival of this droplet at the outlet extremity of the droplet microchannel and/or by controlling the distance between two successive single droplets in said flow of droplets, and
   means for synchronizing the flow of droplets at the outlet extremity of said droplet microchannel and the relative movement of the collection device with regards to the microfluidic platform in order for a controlled number of droplets exiting the outlet extremity of the microfluidic platform placed in front of one of said receiving areas by said means for moving the collection device and the outlet of the microfluidic platform relative to each other to be collected in this receiving area.

2. The microfluidic device according to claim 1, wherein said flow control means control at least the speed of said flow of droplets.

3. The microfluidic device according to claim 1, wherein said synchronization means synchronize the flow of droplets at the outlet extremity of said droplet microchannel and the movements of the collection device depending on the positions of the receiving areas on said collection device.

4. The microfluidic device according to claim 1, wherein said flow control means comprise means for controlling the pressure of said first fluid in said first fluid microchannel and means for controlling the pressure of said second fluid in said second fluid microchannel.

5. The microfluidic device according to claim 1, wherein said microfluidic platform further comprises a reagent microchannel fed with a chemical or biological reagent, the reagent microchannel leading into said first fluid microchannel, upstream from the intersection between this first fluid microchannel and said second fluid microchannel, and wherein said flow control means comprise means for controlling the pressure of said reagent in said reagent microchannel.

6. The microfluidic device according to claim 1, wherein said droplet microchannel is fluidly connected to a capillary and the end of which forms the outlet extremity of the droplet microchannel for the distribution of the flow of droplets.

7. The microfluidic device according to claim 1, wherein said first fluid comprises a plurality of particles, each droplet encapsulating one or zero of these particles.

8. The microfluidic device according to claim 1, wherein each droplet of said flow of single droplets is produced by a transient variation of pressure of at least one of said first and second fluids in said first or second microchannel.

9. The microfluidic device according to claim 5, wherein each droplet of said flow of single droplets is produced by a transient variation of pressure of at least said reagent in said reagent microchannel.

10. Device for the collection and study of living cells, multicellular organisms, or microorganisms from a suspension of said cells, multicellular organisms, or microorganisms in a first fluid, said device comprising at least one microfluidic device according to claim 1, and wherein said microfluidic device is located within a controlled atmosphere enclosure.

11. Method for producing and collecting isolated droplets of a first fluid using a microfluidic device for the production and collection of droplets of a first fluid, said device comprising:
a microfluidic platform comprising:
a first fluid microchannel fed with said first fluid, and a first fluid inlet in fluid communication with the first fluid microchannel;
a second fluid microchannel fed with a second fluid immiscible with said first fluid, and a second fluid inlet in fluid communication with the second fluid microchannel, wherein the second fluid microchannel splits into two fluid microchannels, and then said two fluid microchannels converge and intersect with the first fluid microchannel; and
a droplet microchannel,
said first fluid microchannel and second fluid microchannel intersecting at an inlet extremity of said droplet microchannel and communicating with said droplet microchannel in order to merge said first and second fluids,
wherein is produced within said droplet microchannel of the microfluidic platform a flow of single droplets of said first fluid dispersed in said second fluid immiscible with the first fluid,
said droplet microchannel also comprising an outlet extremity for the distribution of said flow of droplets exiting the droplet microchannel,
a collection device positioned separate and outside of the microfluidic platform, comprising a plurality of receiving areas adapted to collect at least one of said droplets exiting the droplet microchannel through the outlet extremity,
means for moving the collection device and all of its plurality of receiving areas and the outlet of the microfluidic platform relative to each other, in order to place said outlet in front of one of said plurality of receiving areas,
means for controlling the flow of droplets by controlling the time elapsed between the production of a given single droplet and the arrival of this droplet at the outlet extremity of the droplet microchannel and/or by controlling the distance between two successive single droplets in said flow of droplets, and
means for synchronizing the flow of droplets at the outlet extremity of said droplet microchannel and the relative movement of the collection device with regards to the microfluidic platform in order for a controlled number of droplets exiting the outlet extremity of the microfluidic platform placed in front of one of said receiving areas by said means for moving the collection device and the outlet of the microfluidic platform relative to each other to be collected in this receiving area,
said method comprising the steps of:
a) feeding a first microchannel of a microfluidic platform of said microfluidic device with said first fluid,
b) feeding a second microchannel of said microfluidic platform with a second fluid immiscible with the first fluid,
c) producing, in the droplet microchannel of said microfluidic platform a controlled flow of single droplets of said first fluid dispersed in said second fluid by merging said first and second fluid at the intersection (I) of said first fluid and second fluid microchannels with said droplet microchannel,
d) distributing the flow of droplets at the outlet extremity of said droplet microchannel,
e) positioning the collection device of said microfluidic device under the outlet extremity of the droplet microchannel, the collection device and the microfluidic platform being in movement relative to each other,
f) synchronizing the flow of droplets arriving at said outlet extremity of the droplet microchannel with the relative movements of the collection device.

12. The method according to claim 11, further comprising the step of controlling the time elapsed between the production of a given single droplet and the arrival of this droplet at said outlet extremity of the droplet microchannel.

13. The method for studying and collecting particles from a suspension of said particles in a first fluid, comprising the steps of:
producing isolated droplets of said first fluid in a microfluidic device, the dilution of the first fluid being controlled so that each droplet encloses a controlled number of particles, and
collecting the droplets in the collection device, said steps being performed according to the method of claim 11.

14. The method according to claim 13, further comprising the step of introducing a reagent into said first fluid microchannel, upstream from the intersection (I) between this first fluid microchannel and said second fluid microchannel.

15. The method according to claim 14, further comprising the step of controlling the time elapsed between:
the moment when a particle is put in contact with the reagent by introduction of said reagent in said first fluid microchannel, and
the formation of a droplet comprising said particle by merging of said first and second fluid.

16. The method according to claim 14, wherein said particles are cells and said reagent is a cell lysis agent and/or a reverse transcriptase enzyme.

17. The method for studying and collecting particles from a suspension of said particles in a first fluid, comprising the steps of:
producing isolated droplets of said first fluid in a microfluidic device, the dilution of the first fluid being controlled so that each droplet encloses a controlled number of particles, and
collecting the droplets in the collection device,
said steps being performed according to the method of claim 12.

18. The method according to claim 15, wherein said particles are cells and said reagent is a cell lysis agent and/or a reverse transcriptase enzyme.

19. The microfluidic device according to claim 1, wherein said synchronization means synchronize the flow of droplets at the outlet extremity of said droplet microchannel and the movements of the collection device in order for a single droplet to be collected in each of the receiving areas of the collection device.

20. The microfluidic device according to claim 1, wherein said synchronization means ensure that, during the time between the reception of a first droplet in a first receiving area of the collection device and the reception of a second droplet, the collection device is moved from a position where the outlet extremity of the droplet microchannel of the microfluidic platform faces said first receiving area to a position where the outlet extremity of the droplet microchannel faces a second receiving area distinct from the first receiving area.

21. The microfluidic device according to claim 1, wherein the two fluid microchannels converge and intersect with the first fluid microchannel and with the droplet microchannel, at the same location.

22. The microfluidic device according to claim 1, wherein the two fluid microchannels intersect with the droplet microchannel at a direction that is perpendicular to the droplet microchannel.

23. The microfluidic device according to claim 1, wherein said first inlet opening and said second inlet opening are open to an exterior surface of the platform.

24. The microfluidic device according to claim 1, wherein in the means for moving the collection device and all of its plurality of receiving areas and the outlet of the microfluidic platform relative to each other, the microfluidic platform remains fixed and the collection device is moved.

25. The microfluidic device according to claim 1, wherein the means for moving the collection device and all of its plurality of receiving areas and the outlet of the microfluidic platform relative to each other comprise translation means of the collection device and translation control means of an electronic command unit.

26. The microfluidic device according to claim 1, wherein
said collection device is a microtiter plate and said receiving areas are wells of the microtiter plate,
said means for moving the collection device and all of its plurality of receiving areas and the outlet of the microfluidic platform relative to each other comprise a translation stage on which the microtiter plate is placed and a translation controller of an electronic command unit.

27. The microfluidic device according to claim 26, wherein said synchronizing means are programmed to synchronize the translation stage displacement with the frequency of generation of the droplets.

28. The microfluidic device according to claim 27, wherein said synchronization means ensure that, during the time between reception of a first droplet in a first well of the microtiter plate and the reception of a second droplet, the microtiter plate is moved from a position where the outlet of the microfluidic platform faces said first well to a position where the outlet faces a second well distinct from the first well.

* * * * *

SEQUENCE LISTING

```
<160> NUMBER OF SEQ ID NOS: 3

<210> SEQ ID NO 1
<211> LENGTH: 26
<212> TYPE: DNA
<213> ORGANISM: artificial sequence
<220> FEATURE:
<223> OTHER INFORMATION: primer

<400> SEQUENCE: 1
aagcagtggt atcaacgcag agtact                                          26

<210> SEQ ID NO 2
<211> LENGTH: 30
<212> TYPE: DNA
<213> ORGANISM: artificial sequence
<220> FEATURE:
<223> OTHER INFORMATION: primer

<400> SEQUENCE: 2
aagcagtggt atcaacgcag agtacgcggg                                      30

<210> SEQ ID NO 3
<211> LENGTH: 23
<212> TYPE: DNA
<213> ORGANISM: artificial sequence
<220> FEATURE:
<223> OTHER INFORMATION: primer

<400> SEQUENCE: 3
aagcagtggt atcaacgcag agt                                             23
```